(12) United States Patent
Baumgart et al.

(10) Patent No.: US 10,470,732 B2
(45) Date of Patent: Nov. 12, 2019

(54) SYSTEM AND METHOD FOR GENERATING A TIME-ENCODED BLOOD FLOW IMAGE FROM AN ARBITRARY PROJECTION

(71) Applicant: Siemens Medical Solutions USA, Inc., Malvern, PA (US)

(72) Inventors: John Baumgart, Hoffman Estates, IL (US); Martin Trini, Schaumburg, IL (US)

(73) Assignee: Siemens Healthcare GmbH, Erlangen (DE)

( * ) Notice: Subject to any disclaimer, the term of this patent is extended or adjusted under 35 U.S.C. 154(b) by 86 days.

(21) Appl. No.: 14/502,057

(22) Filed: Sep. 30, 2014

(65) Prior Publication Data

US 2016/0089095 A1    Mar. 31, 2016

(51) Int. Cl.
*A61B 6/00* (2006.01)
*G06T 7/00* (2017.01)
*G06T 11/00* (2006.01)

(52) U.S. Cl.
CPC ............ *A61B 6/504* (2013.01); *A61B 6/4441* (2013.01); *A61B 6/481* (2013.01); *G06T 7/0016* (2013.01); *G06T 11/008* (2013.01); *G06T 2207/10016* (2013.01); *G06T 2207/10076* (2013.01); *G06T 2207/10124* (2013.01); *G06T 2207/20224* (2013.01); *G06T 2207/30104* (2013.01); *G06T 2211/404* (2013.01)

(58) Field of Classification Search
CPC ....... A61B 6/4441; A61B 6/481; A61B 6/504; G06T 7/0016; G06T 11/008; G06T 2207/10016; G06T 2207/10076; G06T 2207/10124; G06T 2211/404; G06T 2207/20224; G06T 2207/30104
See application file for complete search history.

(56) References Cited

U.S. PATENT DOCUMENTS

| | | | | |
|---|---|---|---|---|
| 7,187,792 | B2* | 3/2007 | Fu ........................ | A61N 5/1049 382/128 |
| 7,231,076 | B2* | 6/2007 | Fu ........................ | G06K 9/3233 378/4 |
| 7,327,865 | B2* | 2/2008 | Fu ........................... | G06K 9/32 378/28 |
| 8,643,642 | B2* | 2/2014 | Mistretta .............. | A61B 6/4441 345/419 |
| 8,654,119 | B2* | 2/2014 | Mistretta .................. | A61B 6/02 345/419 |
| 8,768,031 | B2* | 7/2014 | Mistretta .............. | A61B 6/4441 382/128 |

(Continued)

OTHER PUBLICATIONS

Copeland et al., "Spatio-Temporal Data Fusion for 3D+T Image Reconstruction in Cerebral Angiography", 2010, IEEE Transactions on Medical Imaging, vol. 29, No. 6, 1238-1251.*

(Continued)

*Primary Examiner* — Katrina R Fujita

(57) ABSTRACT

A system and method include reception of 3D imaging data showing blood flow over time in a patient volume including vessels, reception of a user input of a projection angle, generation of a plurality of 3D images based on the 3D imaging data, generation of a 2D digitally reconstructed radiograph (DRR) at the projection angle input by the user for one of the plurality of 3D X-ray images, and display of the 2D DRR image. Numerous other aspects are provided.

15 Claims, 6 Drawing Sheets

(56) References Cited

U.S. PATENT DOCUMENTS

| | | | |
|---|---|---|---|
| 8,874,187 B2 * | 10/2014 | Thomson | A61B 6/037 378/62 |
| 2003/0181809 A1 * | 9/2003 | Hall | A61B 6/12 600/425 |
| 2006/0072799 A1 * | 4/2006 | McLain | G06T 5/009 382/128 |
| 2011/0235885 A1 | 9/2011 | Rauch et al. | |

OTHER PUBLICATIONS

Mistretta et al., "4D-DSA and 4D fluoroscopy: preliminary implementation", Proc. SPIE 7622, Medical Imaging 2010: Physics of Medical Imaging, 762227.*

Chen et al. "4D CT simulation." Image-Guided IMRT. Springer Berlin Heidelberg, 2006. 247-257.*

Davis, B., et al. "4d digital subtraction angiography: Implementation and demonstration of feasibility." American Journal of Neuroradiology 34.10 (2013): 1914-1921.

* cited by examiner

SYSTEM AND METHOD FOR GENERATING A TIME-ENCODED BLOOD FLOW IMAGE FROM AN ARBITRARY PROJECTION

BACKGROUND

Field

The embodiments described below relate to the processing of angiographic X-ray images acquired while contrast medium is present within a patient volume.

Description

According to conventional angiographic X-ray imaging, a contrast medium is used to enhance the contrast of blood-carrying structures within patient anatomy. For example, a contrast agent is introduced into a patient volume (e.g., via intravenous injection) and an X-ray image of the volume is acquired while the medium is located within the volume. In the X-ray image, structures which contain the agent appear darker than they would otherwise appear.

According to DSA (Digital Subtraction Angiography), a "mask image" of the patient volume is subtracted from an X-ray image acquired as described above. The mask image is acquired without the presence of the contrast medium and represents background anatomic detail. The resulting image is intended to portray only the vessel and perfuse tissue components of the patient volume which include contrast medium.

Two-dimensional (2D) DSA images show a series of images from a particular projection angle. Often, however, it will be advantageous to view this information from several different angles, which may require additional 2D DSAs. However, sometimes patients have difficulty tolerating the contrast medium, either due to allergies or other medical problems (e.g., renal insufficiency). Radiation exposure is a concern and there is a strong desire not to acquire additional X-ray images. In these cases, obtaining additional DSA images is not desirable, even if a different imaging orientation is found that provides a better assessment of the anatomy under scrutiny.

To address the foregoing, a physician either chooses to use existing images or chooses to acquire new images and subject the patient to additional contrast medium injection and X-ray radiation. Known systems therefore involve compromise and use of sub-optimal images or subjection of a patient to additional contrast medium and X-ray radiation.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated for carrying out the described embodiments. Various modifications, however, will remain readily apparent to those in the art.

Those in the art will appreciate that various adaptations and modifications of the above-described embodiments can be configured without departing from the scope and spirit of the claims. Therefore, it is to be understood that the claims may be practiced other than as specifically described herein.

Some embodiments may include generation of a visually (e.g., color) coded static, time-encoded 2D image that depicts 3D data representing blood flow over time from an arbitrary projection angle of the 3D data. The blood may carry a contrast medium used to help identify the path of the blood over time. Since the blood is carrying the contrast medium, it is possible to obtain an image of the blood flow in a particular patient vessel at a particular time from a particular angle. A 4D image, where the fourth dimension (D) is time, may be represented by a series of 3D image volumes, where each volume shows the vessels filled at a given time. In some embodiments, a user is able to rotate the 3D image to view the vessel at a particular projection angle, and create a static 2D image snap-shot from that projection angle. In some embodiments, static, time-encoded 2D images are compared to other static-time encoded 2D images to diagnose patient conditions, to treat patient conditions or to determine efficacy of treatment, or for post-treatment documentation, for example.

Figure 1:
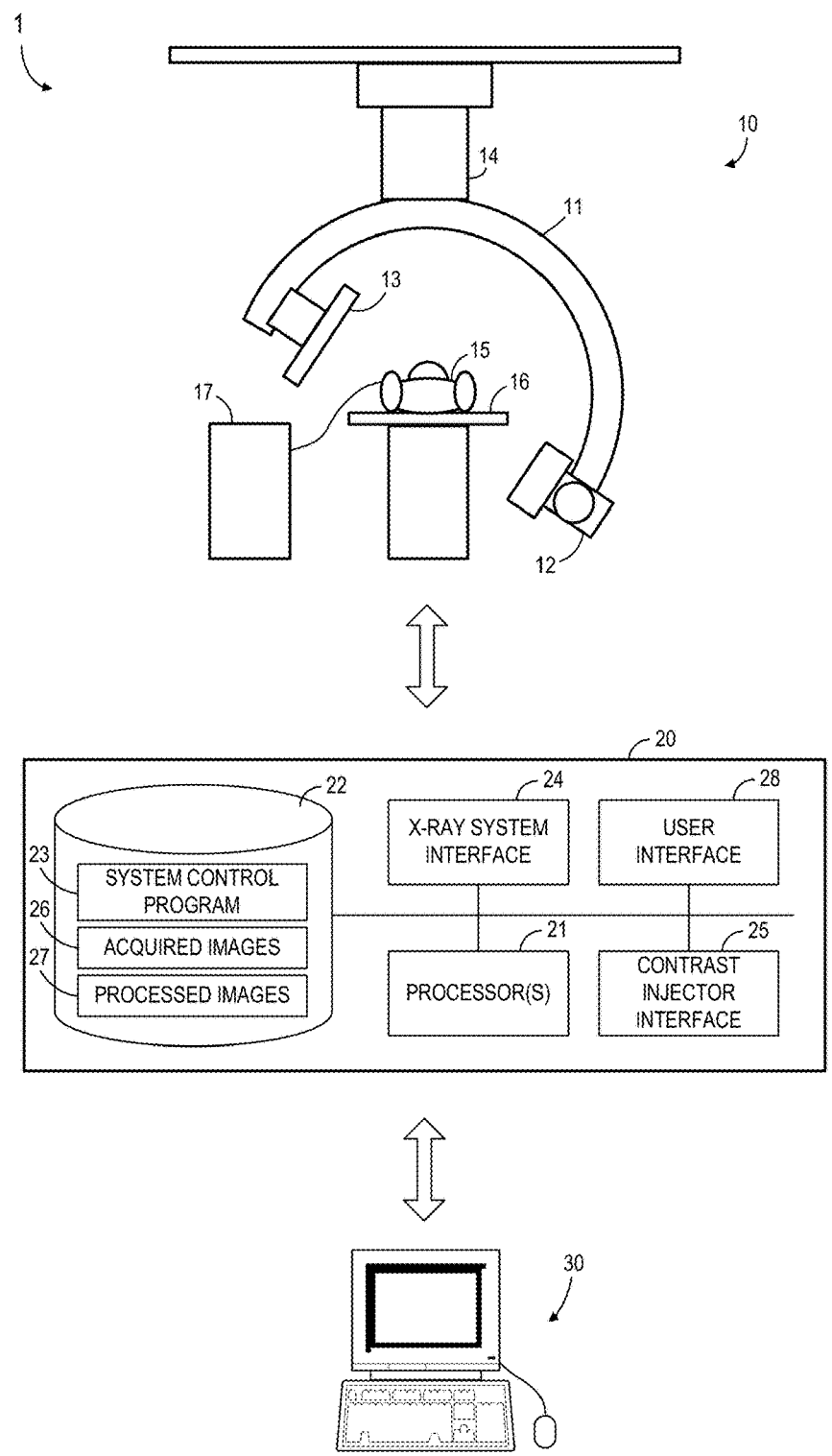
FIG. 1 illustrates a system according to some embodiments.

FIG. 1 illustrates a system 1 according to some embodiments. System 1 includes an X-ray imaging system 10, a control and processing system 20, and an operator terminal 30. Generally, according to some embodiments, the X-ray imaging system 10 introduces contrast medium into a patient volume and acquires X-ray images of the patient volume. The control and processing system 20 controls the X-ray imaging system 10 and receives the acquired images therefrom. The control and processing system 20 processes the images as described below and provides the processed images to a terminal 30 for display thereby. Such processing may be based on user input received by the terminal 30 and provided to the control and processing system 20 by terminal 30.

X-ray imaging system 10 comprises a C-arm 11 on which a radiation source 12 and a radiation detector 13 are mounted. The C-arm 11 is mounted on a support 14 and is configured to translate clockwise or counter-clockwise with respect to the support 14. This translation rotates the radiation source 12 and the radiation detector 13 around a central volume while maintaining the physical relationship therebetween. Embodiments are not limited to C-arm-based imaging systems.

The radiation source 12 may comprise any suitable radiation source, including but not limited to a Siemens Gigalix™ X-ray tube. In some embodiments, the radiation source 12 emits electron, photon, or other type of radiation having energies ranging from 50 to 150 keV.

The radiation detector 13 may comprise any system to acquire an image based on received X-ray radiation. In some embodiments, the radiation detector 13 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In other embodiments, the radiation detector 13 converts received photons to electrical charge without requiring a scintillator layer. The photons are absorbed directly by an array of amorphous selenium photoconductors. The photoconductors convert the photons directly to stored electrical charge. The radiation detector 13 may comprise a CCD or tube-based camera, including a light-proof housing within which are disposed a scintillator, a mirror, and a camera.

The charge developed and stored by the radiation detector 13 represents radiation intensities at each location of a radiation field produced by X-rays emitted from the radiation source 12. The radiation intensity at a particular location of the radiation field represents the attenuated properties of tissues lying along a divergent line between the radiation source 12 and the particular location of the radiation field.

A contrast injector 17 may comprise any known device or devices suitable to controllably introduce contrast medium into a patient volume. As described above, structures which contain contrast medium appear darker in X-ray images than they would otherwise appear. The contrast injector 17 may include a reservoir for each of one or more contrast media, and a patient interface such as medical-grade tubing terminating in a hollow needle.

The system 20 may comprise any general-purpose or dedicated computing system. Accordingly, the system 20 includes one or more processors 21 configured to execute processor-executable program code to cause the system 20 to operate as described herein, and a storage device 22 for storing the program code. The storage device 22 may comprise one or more fixed disks, solid-state random access memory, and/or removable media (e.g., a thumb drive) mounted in a corresponding interface (e.g., a USB port).

It is to be appreciated that at least a portion of the components shown in FIG. 1 may be implemented in various forms of hardware, software or combinations thereof, e.g., one or more digital signal processors with associated memory, application-specific integrated circuits, functional circuitry, etc. It should also be noted that some or all of the system 20, for example, can be incorporated in an application specific or general-use integrated circuit. For example, one or more method steps described below with respect to FIG. 2, or elsewhere, could be implemented in hardware in an application specific integrated circuit (ASIC) rather than using software.

The storage device 22 stores program code of a system control program 23. One or more processors 21 may execute the system control program 23 to move the C-arm 14, to cause the radiation source 12 to emit radiation, to control the detector 13 to acquire an image, to cause the injector 17 to introduce contrast medium into a volume of a patient 15, and to perform any other function. In this regard, the system 20 includes an X-ray system interface 24 and a contrast injector interface 25 for communication with the system 10.

Images acquired from the system 10 are stored in the data storage device 22 as acquired images 26, in DICOM or another data format. Each acquired image 26 may be further associated with details of its acquisition, including but not limited to imaging plane position and angle, imaging position, radiation source-to-detector distance, patient anatomy imaged, patient position, contrast medium bolus injection profile, X-ray tube voltage, image resolution and radiation dosage.

Processor(s) 21 may execute the system control program 23 to process acquired images 26, resulting in one or more processed images 27. Processed images 27 may be provided to the terminal 30 via a user interface 28 of system 20. The user interface 28 may also receive input from the terminal 30, which is used to control processing of acquired images 26 as described below.

The terminal 30 may simply comprise a display device and an input device coupled to the system 20. The terminal 30 displays processed images 27 received from the system 20 and receives user input which may be transmitted to the system 20 and used thereby to generate new processed images 27 for subsequent display by the terminal 30. In some embodiments the terminal 30 is a separate computing device such as, but not limited to, a desktop computer, a lap-top computer, a tablet computer, and a smartphone.

Each of the system 10, the system 20 and the terminal 30 may include other elements which are necessary for the operation thereof, as well as additional elements for providing functions other than those described herein.

According to the illustrated embodiment, the control and processing system 20 controls the elements of the X-ray imaging system 10. The control and processing system 20 also processes images received from the X-ray imaging system 10. Moreover, the system 20 receives input from the terminal 30 and provides processed images to the terminal 30. Embodiments are not limited to a single system performing each of these functions. For example, X-ray imaging system 10 may be controlled by a dedicated control system, with the acquired images being provided to a separate imaging processing system over a computer network or via a physical storage medium (e.g., a DVD).

Figure 2:
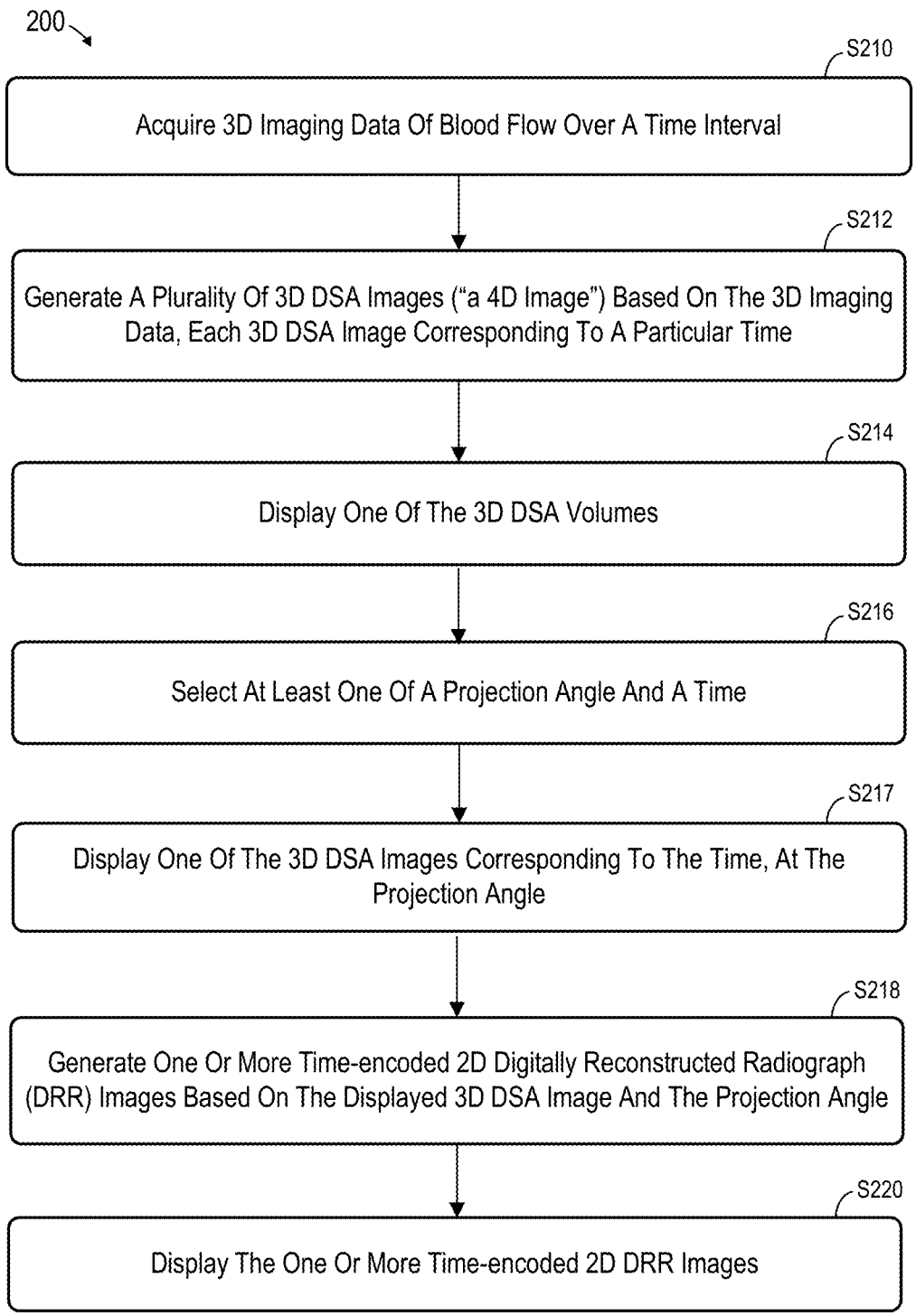
FIG. 2 is a flow diagram of a process according to some embodiments.

Turning to FIGS. 2-6, in one example of operation according to some embodiments, FIG. 2 is a flow diagram of process 200 according to some embodiments. Process 200 and the other processes described herein may be performed using any suitable combination of hardware (e.g., circuit(s)), software or manual means. In one or more embodiments, the control and processing system 20 is conditioned to perform the process 200, such that the processing system 20 is a special purpose element configured to perform operations not performable by a general purpose computer or device. Software embodying these processes may be stored by any non-transitory tangible medium including a fixed disk, a floppy disk, a CD, a DVD, a Flash drive, or a magnetic tape. Examples of these processes will be described below with respect to the elements of system 20, but embodiments are not limited thereto.

Initially, at S210, 3D imaging data showing blood flow over time is acquired, per a time interval defined by a user at the user interface 28, for example. Conventionally, the 3D imaging data is synthesized from a plurality of 2D images, where each 2D image is taken at a particular projection angle over the time interval. For example, prior to contrast medium being introduced into the patient, the radiation source 12 and radiation detector 13 rotate about the patient and acquire 2D images from different projection angles during the rotation, as further described below. In one or more embodiments, a plurality of stationary radiation sources and detectors may acquire the 2D images from different projection angles at substantially the same time. Each of the 2D images taken prior to contrast medium may be referred to as a "mask image."

Then, contrast medium is introduced to the patient, and 2D images are acquired from the same projection angles as the 2D mask images over the time interval. The mask images are then subtracted from each of the respective contrast medium images to form a set of 2D DSA images. The set of 2D DSA images may be used to generate one 3D DSA image (3D imaging data), in one or more embodiments. In one or more embodiments, for example, the 3D DSA may be generated using images or projections obtained after a C-arm rotational acquisition done before (mask run) and after (fill run) the injection of contrast medium. In one or more embodiments, this 3D DSA volume may be referred to as a "constraining volume". The 3D DSA image may be associated with the time interval over which its constituent 2D (non-mask) images were acquired.

In some embodiments of S210, the patient 15 is positioned on the table 16 to place a particular volume of patient 15 between the radiation source 12 and the radiation detector 13. The table 16 may be adjusted to assist in positioning the patient volume as desired. The control and processing system 20 then instructs the X-ray imaging system 10 to move the C-arm 11 so that the radiation source 12 and the radiation detector 13 will generate an image of the patient volume from each projection angle during a time interval set by a user. In some embodiments, X-ray imaging system 10 moves the C-arm 11, and therefore the radiation source 12 and the radiation detector 13, such that the radiation source 12 and the radiation detector 13 rotate about the patient 15. In some embodiments, 180-200 images are acquired over a total period of 8 seconds (e.g., 25 frames per second, or a 40 msec increment per frame), which may correspond to the amount of time needed for contrast medium to flow into and out of the vessels in the brain. The digital storage device 22 stores the 3D image data representing a 3D imaging volume including vessels in the presence of a contrast medium.

In some embodiments, the control and processing system 20 instructs the contrast injector 17 to introduce contrast medium into the patient volume. The radiation source 11 is powered by a high-powered generator to emit X-ray radiation toward the radiation detector 13 at successive intervals before, during, and after introduction of the contrast medium into the patient volume. The parameters of the medium introduction (e.g., flow rate, location, volume) and X-ray radiation emission (e.g., X-ray tube voltage, dosage) may be controlled by a system control program 23 as is known in the art. The radiation detector 13 receives the emitted radiation and processes a set of data (i.e., a projection image) for each interval. The intervals need not be identical in duration.

After the 3D DSA image is generated at S210, the 3D DSA image is processed via the control and processing system 20 using known 4D DSA reconstruction methods in order to generate a plurality of flow-enhanced 3D DSA images at S212. Each of the plurality of flow-enhanced 3D DSA images corresponds to a particular time during the contrast medium injection. The plurality of flow-enhanced 3D DSA images are referred to herein as a 4D DSA image.

One system for creating a 4D DSA image is described in the article "4D Digital Subtraction Angiography: Implementation and Demonstration of Feasibility", *AJNR Am J Neuroradiol* 2013; 1-8, Davis et al., the contents of which are incorporated herein by reference for all purposes. As described therein, the 3D imaging data acquired at S210, which has no specific time dependence, is back-projected into a 3D DSA image based on one of the 2D projection images which was used to create the 3D imaging data. The 2D projection is associated with a particular time, therefore the back-projected 3D DSA image is associated with the particular time. This process is repeated to create additional 3D DSA images based on additional 2D projection images, each of which is associated with a different time. In one or more embodiments, a 3D DSA image depicts an average of the vascular opacification present during the rotational acquisition.

Figure 4A:
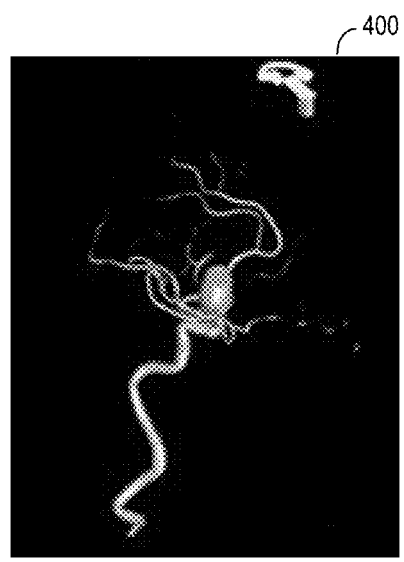
FIGS. 4A and 4B illustrate X-ray images according to some embodiments.
Figure 4B:
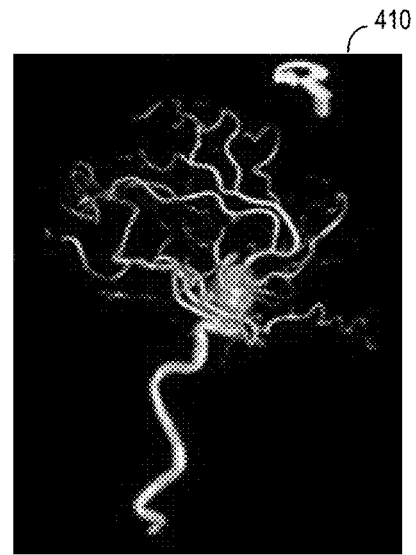

In one or more embodiments, the flow-enhanced 3D DSA images show blood flow (via contrast) over time from any viewing angle (projection) of the 3D data. For example, FIGS. 4A and 4B show two 3D DSA images of a 4D DSA image of a vessel structure (e.g., an artery) at different times (shown in grayscale representing a color coded image). Color or another visual attribute (such as shading, hatching, grayscale, highlight or other visual indicator) may be used to present blood/contrast flow information. The artery image 410 shown in FIG. 4B was generated based on 2D projections taken at a later time than the 2D projections used to generate the artery image 400 shown in FIG. 4A, providing more time for the contrast to flow further as shown by a more detailed image of the artery in FIG. 4B.

In some embodiments, the control and processing system 20 advantageously depicts DSA images in which blood/contrast flow information is displayed with varying colors that identify the time at which blood flow has achieved a desired characteristic. For example, in one or more embodiments, a color of each pixel in a 2D image or voxel (a 3D pixel) in a 3D image may represent a time at which the contrast at that pixel/voxel location reached its peak. Additionally, or alternatively, a color of each pixel/voxel may represent at least one of a time at which the contrast first arrived, a time at which the contrast exited, and a time at which the contrast first reached half its maximum. In one or more embodiments, a sub-sampling or subset of the 3D images (e.g., 20-40 images out of 180-200 images) may be used to create the color DSA, resulting in less computations and therefore faster processing. In some embodiments, the sub-sampling is user configurable such that the user can determine the balance of temporal resolution of the images with the computation time. For example, using 20 images to generate the 2D image is faster than using 200 images, but using 200 images may provide a higher temporal resolution and therefore a clearer image.

In S214, the processor 20 operates to display one of the 3D DSA images on interface 300 from an arbitrary projection angle. In one or more embodiments, the user may select a projection angle for the initial display of the 3D DSA image. Next, at S216, the user selects at least one of a projection angle and a time interval by which to view the data via the user interface 28, and one of the 3D DSA images corresponding to the time is displayed, at the projection angle, at S217. In one or more embodiments, the user operates interface 28 in order to rotate the 3D image of the patient vessel about a central axis to select a projection angle from which to view the contrast flow through the vessel.

Figure 3:
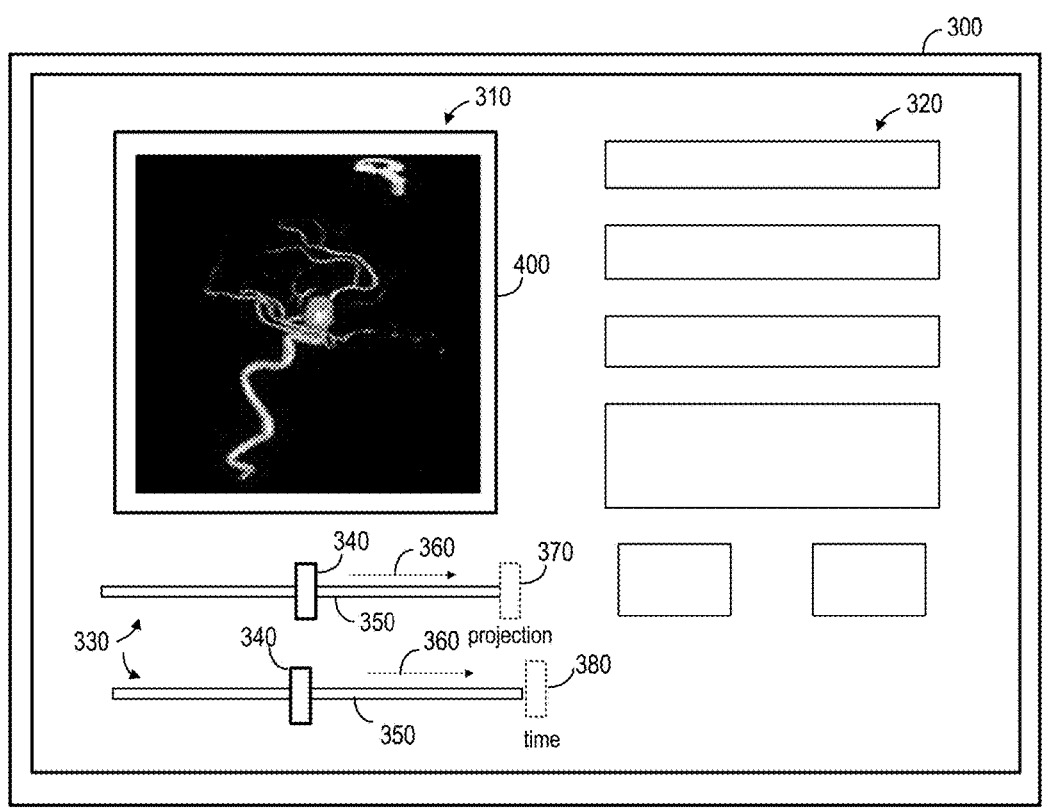
FIG. 3 illustrates a user interface according to some embodiments.

FIG. 3 illustrates interface 300 for displaying a 3D image and for selecting a projection angle and a time interval according to some embodiments. Interface 300 may be displayed by a display device of terminal 30 in response to execution of program code of the system control program 23 by processor(s) 20.

Interface 300 includes area 310 for displaying the 4D volume images. The displayed images may be images generated by the processor 20 based on images acquired by imaging system 10. For example, area 310 of FIG. 3 shows the 3D DSA volume image 400 shown in FIG. 4A.

Interface 300 also includes areas 320 for displaying any suitable information that is or becomes known. For example, the area 320 may present one or more image acquisition parameters (e.g., time interval, sub-sampling, etc.), patient biometric data, or the like. Areas 320 may also or alternatively display information relating to images displayed in area 310, such as, but not limited to, histograms, filtering parameters, and biological information determined based on the images.

Areas 320 may also or alternatively include one or more user interface controls. These controls may allow an operator/user to change the information displayed by the interface 300 or to control image processing performed by system 20, or to perform any other suitable operation.

In this regard, an operator/user operates control 330 in some embodiments to select the projection angle. Additionally, or alternatively, the control 330 may be operated by an operator/user to select the time interval corresponding to the flow of contrast through a vessel. In some embodiments, multiple controls 330 are provided. Control 330 consists of slider 340 and slider bar 350. An operator may move slider(s) 340 along slider bar(s) 350 as illustrated by arrow 360(s) to position 370/380 using a touch screen, a mouse, a keyboard or any other input device. The position of the slider 340 is associated with at least one of a particular projection and a time interval for that projection, which is then used to generate 2D images, as described in detail below.

Embodiments are not limited to the content and arrangement discussed above with respect to FIG. 3. Any one or more user interface controls may be used to change the projection discussed herein. Such controls include, but are not limited to, next input boxes, dials, gestures, etc. Moreover, in some embodiments, an operator may transmit projection angles to the system 20 via an input device (e.g., joystick, mouse, touchpad) without the use of any visually manipulable user interface controls. In such embodiments, the only visual feedback of thusly-changed projections may be the resulting changes in the displayed images. In one or more embodiments, an operator or user may transmit projection angles to the system via voice recognition controls. For example, operators in a control room may be tasked with multiple control actions, and shuffling through the images and selecting images by voice may facilitate these tasks.

Returning to process 200, one or more time-encoded 2D digitally reconstructed radiograph (DRR) images are generated in S218 in response to execution of program code of the system control program 23 by the processor(s) 20. The one or more images are generated based on the currently-displayed 3D DSA image (which corresponds to a particular time) and on the selected projection angle. Then, in S220, the generated images are displayed. In one or more embodiments, a 2D DRR is generated for each of the plurality of 3D DSAs at the projection angle input by the user, and the plurality of 2D DRRs are displayed at the terminal 30.

Figure 5:
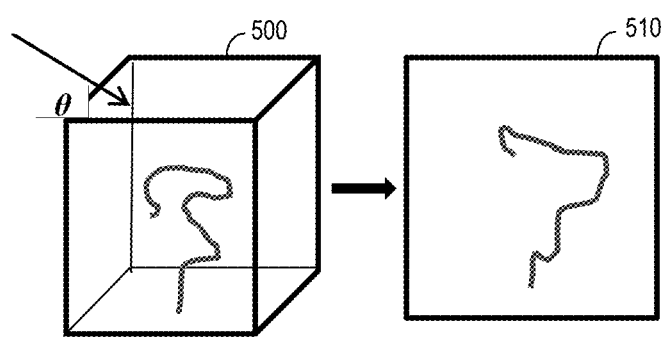
FIG. 5 illustrates X-ray images according to some embodiments.

These images allow the user to see the contrast medium flow through vessels at the selected projection angle at the selected time, although only a single 3D image was acquired at S210 based on a single set of 2D projection images. In some embodiments, a 2D DRR may be reconstructed for each time at a given projection. For example, as shown in FIG. 5, in some embodiments, for each 3D/4D image 500, a 2D DRR 510 is generated at the desired projection angle, θ. The 2D DRR image 510 is representative of what a 2D DSA would look like were a 2D DSA image to have been acquired at the projection at which the DRR image is being generated. The 2D DRR has the same characteristics of a single 2D DSA frame acquired with the radiation source 12 and the radiation detector 13 oriented at projection θ. In one or more embodiments, similar characteristics between a 2D DSA acquired at a specific projection and a synthesized 2D DRR for that same projection may include representation of contrast medium as visually significantly different from the background, a lack of background anatomy, and the same radiographic magnification.

Figure 6:
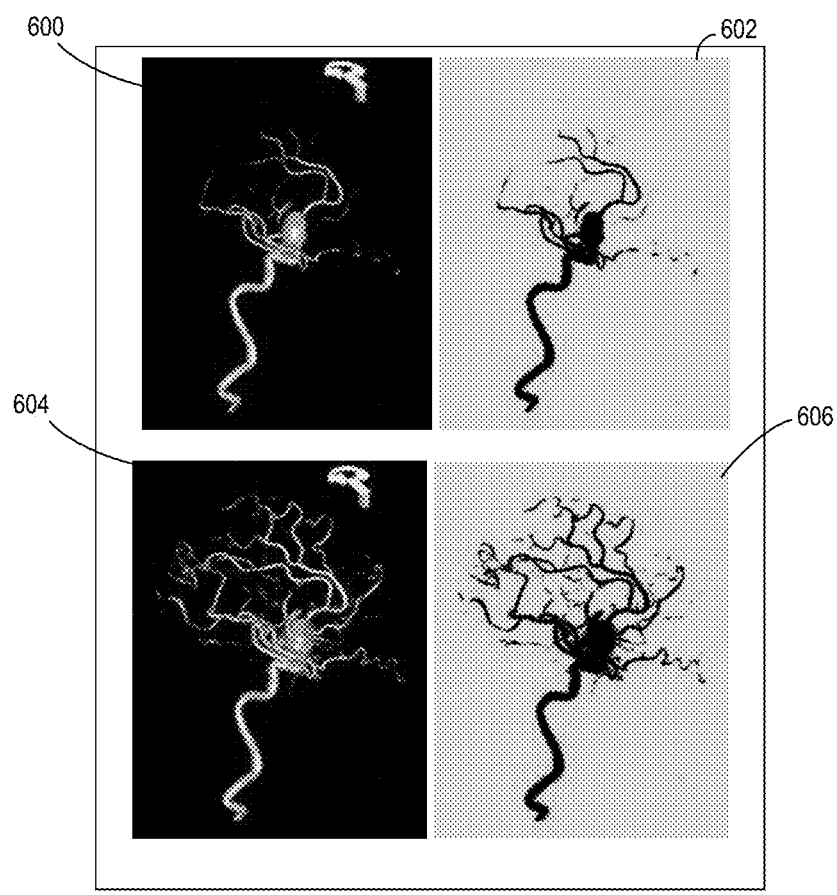
FIG. 6 illustrates X-ray images according to some embodiments.

In one or more embodiments, a series of 2D DRR images for each time interval at a given projection is generated by the processor 20 to show the contrast/blood flow for that time interval. For example, with regard to FIG. 6, 3D volumes at specific times are shown in 600 and 604, with the volume in 604 being acquired at a later time than the volume in 600, as evidenced by the increased detail in 604 as the contrast had more time to flow through the arteries. Images 602 and 606 show 2D DRR images generated from the 3D volumes shown in images 600 and 604, respectively. In FIG. 6, the color or greyscale of each pixel in the 2D DRR image represents, for example, the concentration of contrast at that point at the time represented by the DRR. The time at which the contrast at that location reached its peak may be known or determined by comparing this concentration with the concentration at the same point on the DRR images that represent other times during the injection. In one or more embodiments, additional and/or alternate encodings may indicate attributes such as, for example, the time at which contrast first arrived, the time at which contrast exited, the time at which contrast first reached half its maximum, change in the rate of blood flow. Other suitable alternate encodings may be used.

In one or more embodiments, the processor 20 then uses each of the resulting 2D DRR frames in the series of 2D images to produce a time-encoded composite and static 2D DRR image. In particular, in some embodiments, for example, the series of images forming the 4D volume are used by the processor 20 to generate a composite 2D image showing when the contrast arrived at a particular location (pixel) in the vessel. One of the benefits of static 2D images showing contrast arrival is that it may be helpful to compare static images to see how the blood/contrast flows over time. For example, 2D images of before treatment and after treatment may be compared to determine success of treatment.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising:
an interface to:
receive 3D imaging data showing blood flow over time in a patient volume including vessels;
generate a plurality of 3D images based on the 3D imaging data, wherein each of the plurality of 3D images corresponds to a particular time;
receive a user input of a projection angle and a direct user input of a particular time via manipulation of a time selection control prior to, and for generation of, a time-encoded 2D digitally reconstructed radiograph (DRR); and
an image data processor to:
generate the time-encoded 2D DRR based on one of the plurality of 3D images which corresponds to the particular time and the projection angle input by the user for one of the plurality of 3D images; and
a display to display the time-encoded 2D DRR image.

2. The system of claim 1, wherein the plurality of 3D images are a temporally successive sequence of images.

3. The system of claim 1 wherein the 3D imaging data represents the patient volume in the presence of a contrast agent.

4. The system of claim 3 wherein a color of each pixel of the 2D DRR image represents a time at which the contrast at the pixel location reached its peak.

5. The system of claim 3 wherein a color of each pixel in the 2D DRR image represents at least one of a time at which the contrast first arrived, a time at which the contrast exited, and a time at which the contrast first reached half of its maximum.

6. The system of claim 1 wherein each of the plurality of 3D images is rotatable about a central axis.

7. The system of claim 1 wherein the 3D imaging data comprises an image provided by Digital Subtraction Angiography (DSA) by subtraction of mask image data representing background information from an Angiography image.

8. The system of claim 1, the interface further to:
select a subset of the plurality of 3D images to generate the time-encoded 2D DRR, wherein the subset includes more than one 3D image.

9. The system of claim 1, wherein the interface is further operative to:
display the 3D image at the user input projection angle and direct user input of the particular time prior to generation of the time-encoded 2D DRR.

10. A method comprising:
receiving 3D imaging data showing blood flow over time in a patient volume including vessels;
receiving a user input of a projection angle and a direct user input of a particular time via manipulation of a time selection control prior to, and for generation of, a time-encoded 2D digitally reconstructed radiograph (DRR);
generating a plurality of 3D images based on the 3D imaging data, wherein each of the plurality of 3D images corresponds to the particular time;
generating the time-encoded 2D DRR based on one of the plurality of 3D images which corresponds to the particular time and the projection angle input by the user for one of the 3D images; and
displaying the time-encoded 2D DRR image.

11. The method according to claim 10, wherein the plurality of 3D images are a temporally successive sequence of images.

12. The method according to claim 10, wherein the 3D imaging data represents the patient volume in the presence of a contrast agent.

13. The method according to claim 12, further comprising:
representing, via a color of each pixel in the displayed image, a time at which the contrast reached its peak at the pixel location for the 2D DRR image.

14. The method according to claim 12, further comprising:
representing, via a color of each pixel in the displayed image, at least one of a time at which the contrast first arrived, a time at which the contrast exited, and a time at which the contrast first reached half its maximum.

15. The method according to claim 10, further comprising:
rotating one of the plurality of 3D images about a central axis prior to receiving the user input of the projection angle.

* * * * *